US006468536B1

(12) United States Patent
Panerai et al.

(10) Patent No.: US 6,468,536 B1
(45) Date of Patent: Oct. 22, 2002

(54) USE OF PROTEINS AS ANTI-DIABETES AGENTS

(75) Inventors: Alberto Panerai; Alberto Bartorelli, both of Milan (IT)

(73) Assignee: Zetesis S.p.A., Milan (IT)

( * ) Notice: Subject to any disclaimer, the term of this patent is extended or adjusted under 35 U.S.C. 154(b) by 0 days.

(21) Appl. No.: 09/269,019

(22) PCT Filed: Sep. 17, 1997

(86) PCT No.: PCT/EP97/05079

§ 371 (c)(1),
(2), (4) Date: Apr. 6, 1999

(87) PCT Pub. No.: WO98/11909

PCT Pub. Date: Mar. 26, 1998

(30) Foreign Application Priority Data

| Sep. 18, 1996 | (IT) | MI96A1920 |
| Sep. 18, 1996 | (IT) | MI96A1921 |
| Sep. 18, 1996 | (IT) | MI96A1922 |
| Sep. 18, 1996 | (IT) | MI96A1919 |

(51) Int. Cl.[7] .............................................. A61K 39/00
(52) U.S. Cl. ..................... 424/185.1; 530/350; 530/846
(58) Field of Search ....................... 424/185.1; 530/350, 530/846

(56) References Cited

U.S. PATENT DOCUMENTS 4,024,247 A    5/1977   Fortini et al.

FOREIGN PATENT DOCUMENTS

| WO | 92/10197 | 6/1992 |
| WO | 93/18146 | 9/1993 |
| WO | 96/02567 | 2/1996 |

OTHER PUBLICATIONS

Skolnick et al. Tibtech Jan. 2000 vol. 18, pp. 34–39.*
Ngo et al. The Protein Folding Problem and Tertiary Structure Prediction pp. 492–495, 1994.*
The Merck Manual of Diagnosis and Therapy 17th Edition, pp. 165–177, 416–423, 1474–1476, 1999.*
Journal of Biological Chemistry, vol. 270, No. 50, Dec. 15, 1995, pp. 30060–30067, XP00205817, T. Oka et al "Isolation and Characterisation of Novel Perchloric Acid–Soluble Protein Inhibiting Cell–Free etc.".
European Journal of Biochemistry, vol. 212, No. 3, Mar. 1993, pp. 665–673, XP000673794, Levy–Favatier et al, "Characterization Purification and CDNA Cloning of a Rat Perchloric–Acid–Soluble 23–KDA etc.".

* cited by examiner

*Primary Examiner*—Patrick J. Nolan
(74) *Attorney, Agent, or Firm*—Birch, Stewart, Kolasch & Birch, LLP

(57) ABSTRACT

The use of proteins extracted with perchloric acid from animal organs for the preparation of medicaments active against autoimmune diseases, in particular with activity against atherosclerosis, arthritis, multiple sclerosis, and diabetes.

1 Claim, No Drawings

USE OF PROTEINS AS ANTI-DIABETES AGENTS

This is a 35 USC 371 U.S. national stage application of international application number PCT/EP97/05079, which was filed on Sep. 17, 1997.

The present invention relates to the use of proteins extractable from animal organs, particularly a from livers of mammals, for the preparation of medicaments active against autoimmune diseases, in particular activity against atherosclerosis, arthritis, multiple sclerosis, diabetes.

The administration of complete Freund's adjuvant has proved to be capable of inducing an experimental arthritis very similar to rheumatoid arthritis in rats. On the other hand, the administration of adjuvant to rabbits induces no arthritic pathology, but atherosclerosis. The studies carried out have evidenced that, in both lesions, immunoreactivity to an endogenous factor, which has been identified as the Heat Shock Protein 60 (HSP60), is present. Subsequent searches have confirmed these observations, proving that the administration of complete Preund's adjuvant can be replaced by the administration of HSP60, resulting in the same pathologies. Afterwards, pre-treatment of rat with adjuvant, HSP60 or fragments thereof has proved to prevent the onset of arthritis, with a still obscure mechanism, whereas the administration subsequent to the adjuvant worsens the progress of the disease.

More recently, pre-treatment with adjuvant has been found to also prevent other experimental pathologies which can be defined, generally speaking, as autoimmune disease, such as diabetes or experimental allergic encephalomyelitis (EAE). Finally, HSP60 has been found to have structural analogies to a high number of autoantigens, therefore it is assumed to be related to pathologies more widely than what up to now observed.

WO 92/10197 disclosed protein fractions extractable with perchloric acid from organs of mammals, and their use as anticancer agents. Within these fractions, three main components could be identified, having molecular weights 50, 14 and 10 KDa on gel electrophoresis. The purified extract containing these three components will be referred to as UK 101 in the following. The sequence of the 14 KDa protein component, which is the main, if not the only, responsible for the described activities, is reported in the Table hereinbelow and in WO 96/02567, and it has turned out to be related to that described by other authors (Levy-Favatier, Eur. Biochem. 1903, 212 (3) 665-73) which have assumed that the novel identified sequences belong to the family of the proteins known as chaperoning, to which the HSPs themselves belong.

The proteins described in WO 92/10197 and those of WO 96/02567 (in the following referred to as UK 114) show anyhow properties never observed for chaperonins or analogous proteins. More specifically, it has been found that said proteins can be used in the prevention and in the treatment of autoimmune diseases, in particular atherosclerotic conditions, such as the atherosclerosis induced by organ transplants, arthritis, multiple sclerosis and diabetes.

The invention relates preferably to the use of the purified proteins UK 101 and UK 114 for the preparation of medicaments for the prevention and the treatment of autoimmune diseases such as atherosclerosis following organ transplants, arthritis, multiple sclerosis, diabetes.

Moreover the invention comprises the use of proteins showing a high homology degree to UK 114, of at least 80%, preferably of at least 90%.

ANTIATHEROSCLEROTIC ACTIVITY

It has been ascertained that nowadays the more frequent cause of failure of organ transplants in time is no more the rejection, but the formation of atherosclerotic plaques at the contact point between the vases of the transplanted organ and those of the host. This pathology is worsened by the usual immunosuppressors such as cyclosporin, whereas the use of AZT, which is however very toxic, appears to be useful.

The activity of the proteins UK 101 and UK 114 has been evidenced using both a conventional atherosclerosis model, which is that of the rabbit pre-treated with complete Preund's adjuvant, and a transplant atherosclerosis model. In the first case, the subcutaneous treatment with adjuvant induces within 21 days the formation of atherosclerotic plaques at the iliac bifurcation and at the aortic arch. The pre-treatment (7 days before) with UK 101 or UK 114 has significantly prevented the development of the pathology in a high percent of cases compared with the treatment with the only adjuvant, which has lead to the development of the disease in all of the animals.

On the other hand, the experimental model of transplant atherosclerosis consists in the venous by-passes at the level of arteries in the rat. After a short time, the formation of atherosclerotic plaques at the level of the host vase, as it happens in the human pathology, has been observed. The pre-treatment (7 days before) with UK 101 or UK 114 has significantly prevented the development of the pathology in a high percent of cases, compared with what observed in the animals non pre-treated before the transplant.

ANTIARTHRITIS ACTIVITY

This activity has been evidenced using a conventional arthritis model, which is the adjuvant-induced arthritis. In this model, Lewis rats are injected at the tail base with complete Preund's adjuvant: within 7 days, a pathology at the rear leg appears, characterized by swelling and joints alterations. The pathology reaches its peaks from the 14th to the 21st day, then decreasing until the leg returns to normal conditions. The pre-treatment (7 days before) with UK 101 or UK 114 has significantly prevented the development of the pathology in a high percent of cases compared with treatment with the only adjuvant, which has lead to the development of the pathology in 100% of the animals. The treatment with UK 101 or UK 114 after the administration of adjuvant has worsened the progress of the pathology.

Therefore, it is considered that UK 101 and UK 114 are capable of modifying the progress of or of preventing pathological conditions such as arthritis and rheumatoid arthritis.

ACTIVITY AGAINST MULTIPLE SCLEROSIS

This has been evidenced using a conventional multiple sclerosis model: the experimental allergic encephalomyelitis (EAE). The pathology is induced injecting subcutaneously Lewis rats with a Guinea-pig spinal cord homogenate together with complete Freund's adjuvant. The pathology appears as a progressive paralysis starting from the rear limbs, which begins at about the 12th day, reaches a maximum at about the 21st day and undergoes remission at about the 30th day from the administration of the immunogen. The pre-treatment (7 days before) with UK 101 or UK 114 has significantly prevented the development of the pathology in a high percent of cases and a less serious pathology has appeared, compared with treatment with the only marrow homogenate and adjuvant, which has lead to the development of the pathology in 100% of the animals.

Therefore UK 101 and UK 114 are believed to be able of changing the progress of or preventing pathological conditions such as multiple sclerosis.

ANTIDIABETIC ACTIVITY

This has been evidenced using a conventional diabetes model, represented by the BB rat which spontaneously develops diabetes around the 45th day of life. The animals have been treated at the 30th day of life with UK 101 or UK 114 and the development of the pathology has been observed, compared with untreated control animals. The pre-treatment has been found to decrease the incidence and the severity of the pathology in the experimental model. Some patients affected with tumors at different sites and also suffering from diabetes have been treated with UK 101 in the course of a compassionate treatment with the substance. All of the patients treated, independently of the effect on the tumor pathology, have shown a remission of the diabetic pathology going so far as to quit the insulin therapy.

Therefore UK 101 and UK 114 are believed to be capable of changing the course of diabetes or of preventing it.

The antidiabetic activity has in fact been confirmed, although up to now in a limited number of cases, also n vivo in patients suffering from diabetes.

The proteins of the invention can be administered using suitable formulations, mainly injectable.

The pattern of the administration (doses, frequency of administration, etc.) will be determined according to the circumstances, depending on factors such as conditions of the patient, phase of the disease, etc., but usually a daily dosage ranging from 1 to 100 mg will be suitable.

TABLE

```
Met Ser Glu Asn Ser Glu Glu Pro Val Gly Glu Ala Lys Ala    (SEQ ID NO:1)
1               5                   10

Pro Ala Ala Ile Gly Pro Tyr Ser Gln Ala Val Leu Val Asp
15              20                  25

Arg Thr Ile Tyr Ile Ser Gly Gln Leu Gly Met Asp Pro Ala
    30              35                  40

Ser Gly Gln Leu Val Pro Gly Gly Val Val Glu Glu Ala Lys
        45              50                  55

Gln Ala Leu Thr Asn Ile Gly Glu Ile Leu Lys Ala Ala Gly
            60              65                  70

Cys Asp Phe Thr Asn Val Val Lys Ala Thr Val Leu Leu Ala
                75              80

Asp Ile Asn Asp Phe Ser Ala Val Asn Asp Val Tyr Lys Gln
85              90                  95

Tyr Phe Gln Ser Ser Phe Pro Ala Arg Ala Ala Tyr Gln Val
    100             105                 110

Ala Ala Leu Pro Lys Gly Gly Arg Val Glu Ile Glu Ala Ile
    115             120                 125

Ala Val Gln Gly Pro Leu Thr Thr Ala Ser Val
            130             135
```

---

What is claimed is:

1. A method of treatment for diabetes, comprising administering to an animal in need of such treatment prior to the onset of the diabetes a treatment effective amount of the protein of SEQ ID NO: 1.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 137 amino acids
      (B) TYPE: amino acid
      (C) STRANDEDNESS:
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 1:

Met Ser Glu Asn Ser Glu Glu Pro Val Gly Glu Ala Lys  Ala

-continued

```
1               5                    10
Pro Ala Ala Ile Gly Pro Tyr Ser Gln Ala Val Leu Val Asp
15                  20                  25

Arg Thr Ile Tyr Ile Ser Gly Gln Leu Gly Met Asp Pro Ala
    30                  35                  40

Ser Gly Gln Leu Val Pro Gly Gly Val Val Glu Glu Ala Lys
        45                  50                  55

Gln Ala Leu Thr Asn Ile Gly Glu Ile Leu Lys Ala Ala Gly
            60                  65                  70

Cys Asp Phe Thr Asn Val Val Lys Ala Thr Val Leu Leu Ala
                75                  80

Asp Ile Asn Asp Phe Ser Ala Val Asn Asp Val Tyr Lys Gln
85                  90                  95

Tyr Phe Gln Ser Ser Phe Pro Ala Arg Ala Ala Tyr Gln Val
        100                 105                 110

Ala Ala Leu Pro Lys Gly Gly Arg Val Glu Ile Glu Ala Ile
            115                 120                 125

Ala Val Gln Gly Pro Leu Thr Thr Ala Ser Val
                130                 135
```